United States Patent [19]

Yoshida

[11] Patent Number: 4,555,635
[45] Date of Patent: Nov. 26, 1985

[54] SURFACE FLAW INSPECTION APPARATUS FOR A CONVEX BODY

[75] Inventor: Hajime Yoshida, Chofu, Japan

[73] Assignee: Hajime Industries, Ltd., Tokyo, Japan

[21] Appl. No.: 501,165

[22] Filed: Jun. 6, 1983

[30] Foreign Application Priority Data

Jun. 15, 1982 [JP] Japan .............................. 57-102699

[51] Int. Cl.[4] .......................................... G01N 21/88
[52] U.S. Cl. .................................... 250/572; 356/445
[58] Field of Search ...................... 250/562, 563, 572; 356/237, 371, 445, 448

[56] References Cited

U.S. PATENT DOCUMENTS

| | | | |
|---|---|---|---|
| 3,746,784 | 7/1983 | Van Oosterhout | 250/562 X |
| 4,291,990 | 9/1981 | Takasu | 356/237 X |
| 4,403,858 | 9/1983 | Yoshida | 356/237 |

FOREIGN PATENT DOCUMENTS 115313  7/1983  Japan .................................. 356/371

OTHER PUBLICATIONS

"Detecting Surface Deformities", IBM Technical Disclosure Bulletin, vol. 14, No. 1, Jun. 1971.

Primary Examiner—Shrive P. Beck
Attorney, Agent, or Firm—Murray Schaffer

[57] ABSTRACT

A surface flaw inspection apparatus for a convex body having a light source for irradiating a surface of an object to be inspected with a luminous flux, an image sensor for receiving the reflected light on the surface of the object and producing a corresponding electrical signal, an inspection section for receiving the electrical signal from the image sensor and inspecting whether or not there is a flaw on the surface of the object, and a projection screen located in the light path from the light source through the surface of the object to the image sensor on which an image of the irradiated area of the surface of the object by the luminous flux is formed, in which the image sensor picks up the image formed on the projection screen.

8 Claims, 4 Drawing Figures

SURFACE FLAW INSPECTION APPARATUS FOR A CONVEX BODY

BACKGROUND OF THE INVENTION

1. Field of the Invention

The present invention relates generally to surface flaw inspection apparatuses for convex shaped bodies, and is directed more particularly to such inspection apparatus that avail positive and highly accurate, but still automatic inspections under a simple construction to check the existance or not of surface flaws on convex shaped bodies that have strong reflections (or have high reflectivity) on the surface thereof.

2. Description of the Prior Art

It is an extremely difficult problem to visually check the surface conditions (flaws there or not) on convex body surfaces with high reflectivity, for example, the convex surface of metal bodies that are mirror-finished or where such convex surface is plated. Therefore, in the recent years, various attempts are proposed as systems to automatically inspect whether or not there are such surface flaws as dirty, scratches or the like by photosensing such above described convex surfaces with high reflectivity by such image sensors such as a television camera or the like from which the image signal is electrically processed.

However, the fact remains that such above described flaw inspection on convex surfaces with high reflectivity is still extremely difficult, just like the case of visual inspection, by such presently proposed automatic inspection apparatuses for convex surfaces.

An example of such above described automatic inspection apparatus under the conventional art will be explained in reference with FIG. 1 and FIG. 2. FIG. 1 shows the relation between incident light IL and reflected light RL on the inspected surface which is a convex surface (spherical surface) 2 of a convex body 1 such as a ball, which is the inspected object. As well known, the incident light IL and reflected light RL on, for example, a point P on the convex surface 2, are symmetrical to each other with respect to the normal N to the convex surface 2 at point P. In other words, incident angle $\theta_I$ is equal to reflection angle $\theta_R$.

FIG. 2 is a schematic diagram showing an example of a prior art inspection apparatus which will inspect the convex surface 2 of the convex body 1. On this figure, 3 designates a light source. The incident light IL from such light source 3 to the convex surface 2 of the convex body 1 is reflected on each of points A1, A2, A3 . . . on the convex surface 2 of the convex body 1 and then become reflected lights RL1, RL2, RL3 . . . . In the example on FIG. 2, due to the positions or locations of the light source 3 and a television camera 4, only the reflected light RL1 among the reflected lights is caught by the television camera 4 while the other reflected lights are out of the visual field of the television camera 4. In other words, out of the convex surface or inspected surface 2 of convex body 1, the flaws there or not can only be inspected at point A1. In this case, the reflected light RL1 that is introduced into camera 4, can be said to be the light from light source 3 itself, so that the reflected light RL1 is very strong or intensive which makes it extremely difficult to inspect small flaws at point A1.

Further, in order to totally inspect the inspected surface 2, it will be necessary to slowly rotate the convex body 1 relative to the camera 4 for a full or one rotation.

In addition, since some of the other reflected lights on convex surface 2 at other points than A1 may also enter television camera 4, in the strict sense, it can be said that the conventional example on FIG. 2 may inspect surfaces other than point A1 at the same time, but as long as the inspected surface 2 is a convex surface, no matter how the positioning arrangements between the television camera 4 and the inspected surface 2 as well as the light source 3, are changed, the light beam itself from light source 3 will enter the camera 4 as an image such as in the case at point A1, which causes inspection difficulties.

FIG. 3 shows another prior art example which is proposed in order to avoid such above mentioned defective point. In this example, a plurality of, in the case shown in the figure, two light sources $3_1$ and $3_2$ are used to irradiate the convex surface 2 of the convex body 1 through light diffuser plates $5_1$ and $5_2$, and the television camera 4 placed therebetween is prevented from being directly irradiated upon by the lights from light sources $3_1$ and $3_2$ which are reflected on the convex surface 2 to thereby remove such conventional defect. In other words, with the example shown on FIG. 3, the light beams from light sources $3_1$, $3_2$ are diffused by light diffusers $5_1$ and $5_2$ to irradiate certain areas of the convex surface 2 and the lights reflected thereon are caught by the television camera 4 to inspect such areas of convex surface 2.

However, in this example, such a defect is caused that, as shown on FIG. 3, with respect to point B on the convex surface 2, the image of lens section 4 of the television camera 4 is picked up by the camera 4. In other words, by this prior art apparatus, the normal to point B on the convex surface 2 and the optical axis of the television camera 4 are coincident to each other so that the inspection of the point B on this convex surface 2 is impossible.

Symbol 6 on FIG. 2 and FIG. 3 indicates the inspection system to detect whether there is a flaw or not, such as scratches, etc. on the inspected surface 2 by processing the output image signal from the television camera 4, as well known.

OBJECTS AND SUMMARY OF THE INVENTION

Therefore, it is an object of the present invention to propose a surface flaw inspection apparatus for convex bodies free from the defects inherent in the prior art apparatus.

According to an aspect of the present invention there is provided a surface flaw inspection apparatus for a convex body which comprises:

(a) a light source for irradiating a surface of an object to be inspected with a luminous flux;

(b) an image sensing means for receiving a reflected light on said surface of the object and producing a corresponding electrical signal;

(c) an inspection means for receiving the electrical signal from said image sensing means and inspecting whether or not there is a flaw on the surface of said object; and (d) a projection screen located in a light path from said light source through said surface of the object to said image sensing means on which an image of an irradiated area of the surface of the object by the luminous flux from said light source is formed, said image sensing means picking up the image on said projection screen.

The additional, and other objects, features and advantages of the present invention will become apparent from the following description taken in conjunction with the accompanying drawings.

DESCRIPTION OF THE PREFERRED EMBODIMENT

Figure 1:
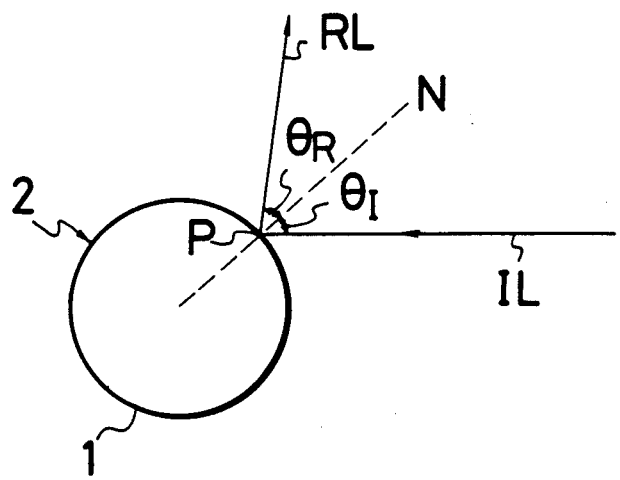
FIG. 1 is a schematic diagram that is used to explain the relation between an incident light beam and its' reflected light on a convex surface.
Figure 2:
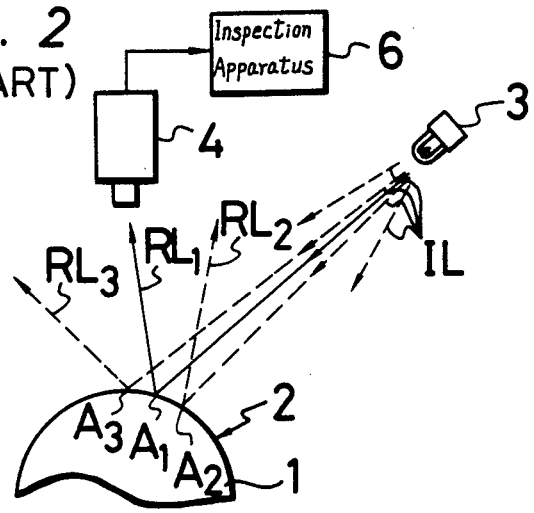
FIG. 2 and FIG. 3 respectively are schematic diagrams showing prior art inspection apparatuses.
Figure 3:
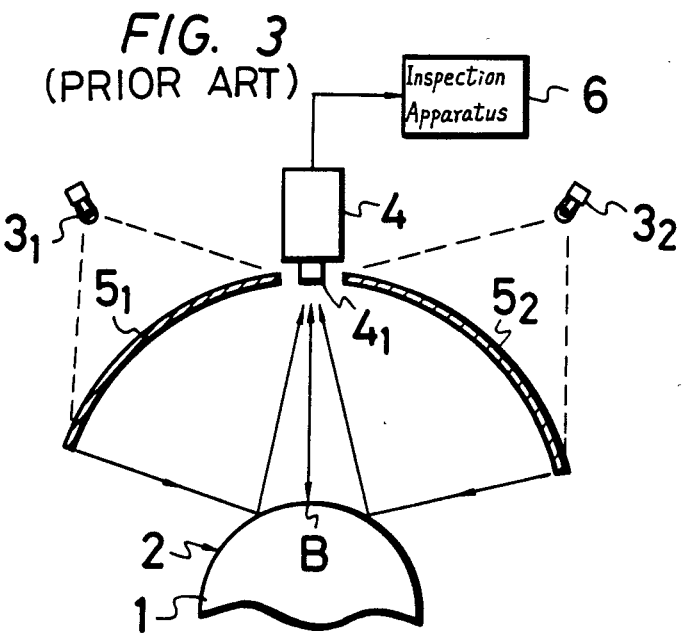

An example of the present invention will be explained hereunder in reference with FIG. 4. On FIG. 4, the same symbols as those shown on FIG. 1 to FIG. 3 indicate the same elements and parts.

Figure 4:
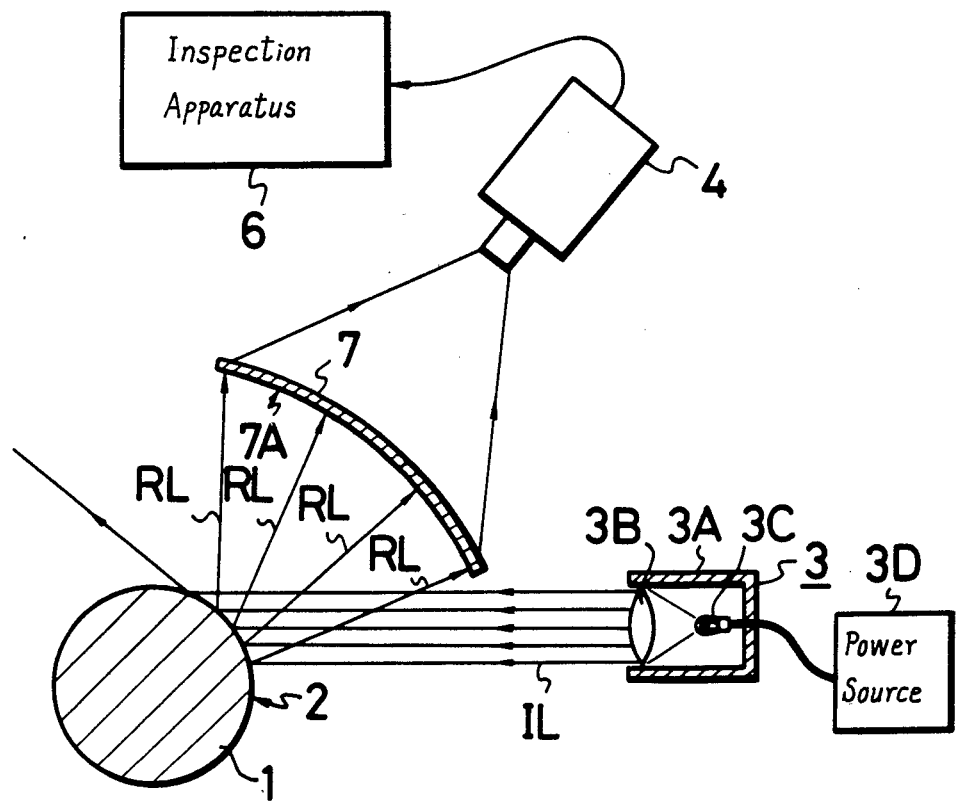
FIG. 4 is a schematic diagram showing one example of the present invention.

Now, in the example of the present invention as shown on FIG. 4, a single light source 3 is employed to emit a substantially parallel light or luminous flux IL which irradiates the inspected object 1 i.e. the inspected surface 2 of the convex body 1 or the convex surface 2 thereof. As shown in the figure, the light source 3 is construed by arranging a light emission body 3C such as a lamp substantially at one focal point of convex lens 3B within a cylindrical body 3A, which one side is closed and the other end of the cylindrical body 3A is open to which the convex lens 3B is fit at the open end. Thus, the light emitted from the light source 3C and passed through the convex lens 3B becomes the luminous flux IL as set forth above. 3D is the power source for lamp 3C.

Between the inspected surface 2 and the image senser such as television camera 4, a transmission type projection screen 7, made of, for example, transparent plastic material or the like is located which is substantially uniform in thickness. On the surface of this transmission type projection screen 7 which counter faces the inspected surface 2, is formed an image forming surface 7A such as a delustering surface on which images are formed by the fact that the light incident on the surface 7A is partially diffused or scattered. Therefore, on this delustering surface 7A of this projection screen 7, formed is the image of an area of the inspected surface 2 irradiated with the parallel luminous flux IL by such a manner that the parallel luminous flux IL from the light source 3 reflects on a predetermined area of the inspection surface 2 and the reflected luminous flux RL thereon is projected onto the delustering surface 7A of the projection screen 7.

Accordingly, it is desireous that the shape or configuration of the transmission type projection screen 7 or its delustering screen 7A be formed so that each of the distances for the reflected luminous fluxes RL at respective points within the irradiated area of the inspected surface 2 to arrive at the delustering surface 7A be equal to each other.

By selecting the configuration of the delustering surface 7A as such, the image of the irradiated area of the inspected surface 2 formed on the delustering surface 7A will be substantially uniform, so that an inspection for flaws on the inspected surface 2 can be conducted effectively.

With the example of the present invention as shown on FIG. 4, image sensor 4 such as a television camera is arranged at the counter side to the inspected body 1 against the projection screen 7, the image of the irradiated area of the inspected surface 2 on the delustering surface 7A is picked up through projection screen 7, and the output from the image sensor 4 is processed at the inspection apparatus 6 similar to the prior art to thereby inspect the existance or not of flaws on the inspected surface 2. Therefore, according to this invention, the television camera 4 will not pick up the image of the light source 3 itself as above mentioned in the case of the prior arts nor photosense the image of the lens section $4_1$ of the television camera 4, so that automatic flaw inspection may be conducted positively and easily even though the object to be inspected be convex bodies such as a ball body, cylindrical body etc. containing convex surface, moreover even with high reflectivities.

In this case, by the present invention, the light source 3 is a single one and the light IL therefrom is not diverged, but rather is luminous flux so that unnecessary light does not directly enter the projection screen 7 nor directly enter the television camera 4.

Further, in the case that the irradiated area of the inspected surface 2 on the inspected body 1 by the parallel luminous flux IL from the light source 3 is a part of the surface 2 to be inspected, it is of course necessary that although not shown on the figure, by a proper drive system the inspected body 1 may be rotated or moved so that all of the inspected surface 2 be consecutively irradiated by parallel luminous flux IL, such consecutive images are formed on delustering surface 7A and then the above mentioned inspection process will be repeated.

Also, the incident angle of the parallel luminous flux IL from the light source 3 on the inspected surface 2 may be varied depending upon the size and carvature of the inspected surface 2. In such case, the shape or configuration of the transmission type projection screen 7 may be modified in correspondence therewith.

In such case, it is needless to say that arrangements be made so that the parallel luminous flux IL from light source 3 does not directly enter the delustering surface 7A of the projection screen 7 nor the image senser 4.

Further, it is not necessary to limit the light source 3 to one that emits parallel luminous flux, but such one may be used which emits luminous flux somewhat diverging or converging in response to the shape and so on of the inspected surface 2.

Further, it is obvious that even if, depending upon the shape of the inspected body 1, in other words the inspected surface 2 thereof, the television camera 4 may be placed at the same side of the projection screen 7 in relation to the inspected body 1 to pick up the image on the delustering surface 7A directly, the same effect can be attained by judging the characteristics of the light source 3 of the present invention. In such case, as for the projection screen 7, besides the transmission type one, a reflection type one may also be used.

It will be apparent that many modifications and variations could be effected by one skilled in the art without departing from the spirits or the scope of the novel concepts of the present invention so that the spirits or scope of the invention should be determined by the appended claims only.

I claim as my invention:

1. Apparatus for inspecting the surface of a convex body for flaws, comprising:
   (a) a light source directly irradiating a surface of an object to be inspected with a substantially parallel light flux, said surface of the object being curved;
   (b) image sensing means receiving the reflected light from said curved surface of the object and producing a corresponding electrical signal;
   (c) inspection means receiving the electrical signal from said image sensing means and determining whether or not there is a flaw on the surface of said object; and
   (d) a projection screen located in the light path from said light source through said curved surface of the object to said image sensing means on which the image of the irradiated area of the curved surface of the object by the parallel light flux from said light source is formed, said projection screen being curved such that each of the distances of reflected light fluxes at the respective points with the irradiated area of said curved surface of the object is substantially equal to each other, said image sensing means picking up the image on said projection screen.

2. A surface flaw inspection apparatus as claimed in claim 1, wherein said light source is a single light source which consists of a light emission element and an optical system.

3. A surface flaw inspection apparatus as claimed in claim 1, wherein said projection screen is made of transparent material and is provided with an image forming surface on its one surface on which said image of the object is formed.

4. A surface flaw inspection apparatus as claimed in claim 2, wherein positional relation among said light source, object, projection screen and image sensing means is so selected that the parallel light flux from said light source never enters said projection screen and image sensing means directly.

5. A surface flaw inspection apparatus as claimed in claim 3, wherein said image forming surface is formed on a surface of said projection screen, said surface opposing the surface of said object to be inspected.

6. A surface flaw inspection apparatus as claimed in claim 5, wherein said image sensing means is located opposite said object with respect to said projection screen so that said image sensing means picks up the image formed on said image forming surface through said projection screen.

7. A surface flaw inspection apparatus as claimed in claim 5, wherein said image sensing means is located at the side same as that of said object with respect to said projection screen so that said image sensing means picks up the image formed on said image forming surface directly.

8. A surface flaw inspection apparatus as claimed in claim 1, wherein a surface of said projection screen opposing the surface of said object is so shaped that distance between respective points of the surfaces of said object and projection screen are substantially equal with one another.

* * * * *